United States Patent
Pote et al.

(10) Patent No.: US 8,107,696 B2
(45) Date of Patent: Jan. 31, 2012

(54) CALIBRATION APPARATUS AND METHOD FOR FLUORESCENT IMAGING

(75) Inventors: Jeffrey Pote, Easton, PA (US); Gregory Payonk, Flanders, NJ (US); Nikiforos Kollias, Skillman, NJ (US); Dick Jackson, Victoria (CA)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 1068 days.

(21) Appl. No.: 11/863,345

(22) Filed: Sep. 28, 2007

(65) Prior Publication Data

US 2008/0080781 A1    Apr. 3, 2008

Related U.S. Application Data

(60) Provisional application No. 60/848,707, filed on Oct. 2, 2006.

(51) Int. Cl.
*G06K 9/00* (2006.01)
(52) U.S. Cl. ........................................ 382/128
(58) Field of Classification Search ............... 382/128, 382/141, 190, 191, 206, 207, 211, 260, 312; 396/14, 15; 362/4, 5, 260, 296.03; 235/455; 250/370.08
See application file for complete search history.

(56) References Cited

U.S. PATENT DOCUMENTS

| | | |
|---|---|---|
| 3,971,065 A | 7/1976 | Bayer |
| 5,016,173 A | 5/1991 | Kenet et al. |
| 5,741,648 A * | 4/1998 | Hemstreet et al. ............ 435/6 |
| 5,778,045 A | 7/1998 | von Stetten et al. |
| 6,125,338 A | 9/2000 | Brienza et al. |
| 6,208,749 B1 | 3/2001 | Gutkowicz-Krusin et al. |
| 6,993,167 B1 * | 1/2006 | Skladnev et al. ............. 382/128 |
| 7,835,559 B1 | 11/2010 | Schurman et al. |
| 2002/0133080 A1 | 9/2002 | Apruzzese et al. |

(Continued)

FOREIGN PATENT DOCUMENTS

DE   1028804 B   4/1958

(Continued)

OTHER PUBLICATIONS

International Search Report of the International Searching Authority mailed Oct. 24, 2008, issued in connection with International Patent Application No. PCT/US07/80037 (3 pages).

(Continued)

*Primary Examiner* — Jason M Repko
*Assistant Examiner* — Shervin Nakhjavan
(74) *Attorney, Agent, or Firm* — Paul F. Swift

(57) ABSTRACT

A fluorescence standard for identifying variations in illumination during imaging has a composite fluorescent laminar structure, which fluoresces in response to light in the approximate wavelength range of 375 nm to 430 nm. The fluorescent object has at least two areas with different fluorescent response, e.g., a first made from a strongly luminescing material, such as GG420 filter glass. A portion of the GG420 glass is covered by filter glass having an attenuating effect on the fluorescent response. In accordance with a method of the present invention, variations in illumination during imaging with a camera are detected by placing the standard before the camera during imaging. Each captured image may contain the image of the standard and the fluorescent response of the standard in different images can be compared to identify any response changes due to variations in illumination. The variations in illumination can then be remediated by adjusting the source of illumination, the camera or ambient lighting. Alternatively, the images can be normalized through digital image processing.

16 Claims, 2 Drawing Sheets

U.S. PATENT DOCUMENTS

| | | | |
|---|---|---|---|
| 2003/0045916 A1* | 3/2003 | Anderson et al. | 607/89 |
| 2003/0067545 A1* | 4/2003 | Giron et al. | 348/223.1 |
| 2003/0086703 A1 | 5/2003 | Kollias et al. | |
| 2003/0086712 A1 | 5/2003 | Merola et al. | |
| 2003/0138249 A1 | 7/2003 | Merola et al. | |
| 2004/0125996 A1 | 7/2004 | Eddowes et al. | |
| 2004/0146290 A1 | 7/2004 | Kollias et al. | |
| 2004/0196455 A1* | 10/2004 | Ermantraut et al. | 356/243.1 |
| 2004/0252303 A1* | 12/2004 | Giorgianni et al. | 356/402 |
| 2005/0030372 A1* | 2/2005 | Jung et al. | 348/77 |
| 2005/0195316 A1* | 9/2005 | Kollias et al. | 348/370 |
| 2005/0211912 A1* | 9/2005 | Fox | 250/458.1 |
| 2005/0282292 A1* | 12/2005 | Torre-Bueno | 436/180 |
| 2005/0287040 A1* | 12/2005 | Giebeler et al. | 422/82.08 |
| 2006/0013454 A1* | 1/2006 | Flewelling et al. | 382/128 |
| 2006/0060931 A1* | 3/2006 | Cochet et al. | 257/414 |
| 2006/0092315 A1 | 5/2006 | Payonk et al. | |
| 2006/0208199 A1 | 9/2006 | Gallagher et al. | |
| 2008/0038835 A1 | 2/2008 | Westphal et al. | |

FOREIGN PATENT DOCUMENTS

| | | |
|---|---|---|
| DE | 102004047593 A | 4/2006 |
| EP | 0682236 | 11/1995 |
| WO | 97/47235 | 12/1997 |
| WO | 01/35827 | 5/2001 |

OTHER PUBLICATIONS

Written Opinion of the International Searching Authority mailed Oct. 24, 2008, issued in connection with International Patent Application No. PCT/US07/80037 (5 pages).

European Examination Report mailed Mar. 23, 2010, issued in connection with European Patent Application No. 07843581.5 (4 pages).

Barel, et al., "The Visi—Chroma VC-100®; A New Imaging Colorimeter for Dermatocosmetic Research", Skin Research and Technology, 7, 2001, pp. 24-31.

U.S. Appl. No. 12/201,044 entitled "Imaging Standard Apparatus and Method", filed Aug. 29, 2008 (50 pages).

\* cited by examiner

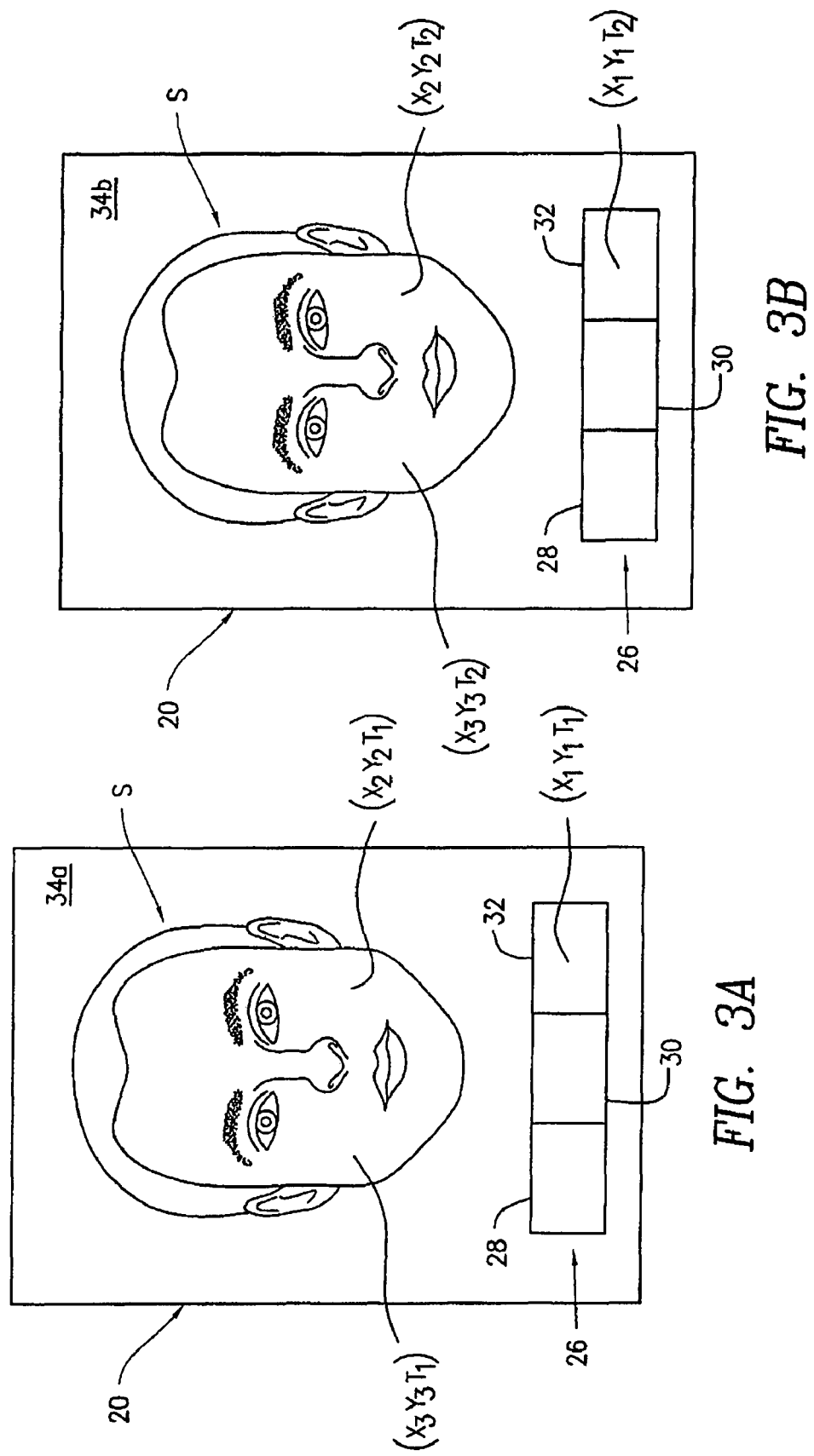

# CALIBRATION APPARATUS AND METHOD FOR FLUORESCENT IMAGING

CROSS-REFERENCE TO RELATED APPLICATIONS

This application claims the benefit of U.S. Provisional Patent Application Ser. No. 60/848,707 filed Oct. 2, 2006, the disclosure of which is incorporated herein by reference in its entirety.

FIELD OF THE INVENTION

The present invention relates to an apparatus and method for calibrating skin imaging systems, and more particularly, for calibrating skin imaging systems in which the skin is photographed under UV and/or blue light resulting in a fluorescent image.

BACKGROUND OF THE INVENTION

Various imaging systems have been proposed that photographically capture images of a person's face for analysis of the health and aesthetic appearance of the skin. Different images, captured at different times or under different lighting conditions can be used and/or compared to one another to gain insight into the condition of the skin and its response to treatment. This was typically done by human operators inspecting the photographs to identify certain visual indicators of skin condition and to ascertain changes between photographs. When the skin is photographed under an illuminating light, such as a flash or strobe light, the light intensity and wavelength of the light can vary from one photograph to another. Environmental lighting conditions can also lead to variations in illuminating light. Variations in illuminating light can result in variations in the digital images captured which are not attributable to skin condition changes, thereby lessening the probative value of digital imaging analysis.

SUMMARY OF THE INVENTION

The problems and disadvantages associated with conventional apparatus used in digital skin imaging are overcome by a fluorescence standard for identifying variations in illumination during imaging conducted at a plurality of times, which includes a fluorescent object that fluoresces in response to light in the approximate wavelength range of 375 nm to 430 nm. The fluorescent object has two areas with different fluorescent response. In accordance with a method of the present invention, variations in illumination during imaging with a camera are detected by placing a fluorescent object, which fluoresces in response to light in the approximate wavelength range of 375 nm to 430 nm before the camera. A first image of the fluorescent object is captured with light in the approximate wavelength range of 375 nm to 430 nm. A second image of the fluorescent object is captured with light in the approximate wavelength range of 375 nm to 430 nm. The fluorescent response of the fluorescent object in the first image is then compared to the fluorescent response of the fluorescent object in the second image.

Other aspects, features and advantages of the present invention will be apparent from the detailed description of the invention that follows.

BRIEF DESCRIPTION OF THE DRAWINGS

FIG. 3A is front view of a first photographic image of a subject and the calibration apparatus, as taken at time T1; and FIG. 3B is front view of a second photographic image of a subject and the calibration apparatus, as taken at time T2.

DETAILED DESCRIPTION OF THE INVENTION

The present invention includes an apparatus and method for calibration of a skin imaging station. The calibration apparatus includes a fluorescence standard with a first layer made of material having fluorescent properties similar to that of skin when exposed to UV and/or blue light. Additional layers made of translucent material that partially overlay the first layer attenuate the fluorescence intensity of the first layer producing a multi-step calibration standard.

In accordance with a method of the present invention, the calibration standard is positioned proximate the subject's face, is photographed with the subject and appears in the same photographic image. On taking a UV or blue fluorescence photograph, the different portions of the calibration standard having different numbers of layers absorb the UV and/or blue light and fluoresce at different, known levels, providing multiple fluorescence standards for calibration. A plurality of digital images are recorded for comparison to each other, each recording the fluorescence intensity for the subject's face and for the standard. The fluorescence values attributable to the standard are compared in subsequent digital images to determine if a variation in intensity has occurred, signaling a variation in illumination brightness. A software routine determines the location of the fluorescence standards in the image. If the light intensity of the illuminating light is determined to have varied, the image may be recaptured by taking another photograph. The illumination intensity may be adjusted prior to taking the replacement image or the photographer may correct environmental factors that led to the variation. Alternatively, the software may adjust the display intensity of the image by adjusting the pixel intensity values to compensate for the variation in illumination intensity.

Figure 1:
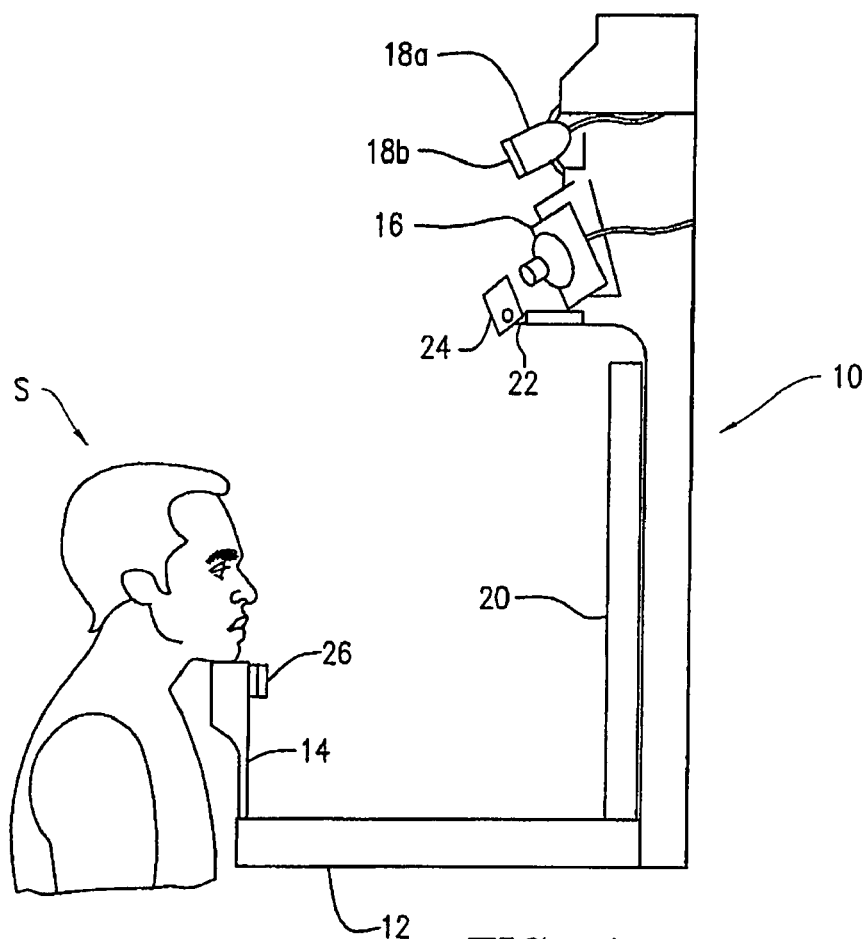
FIG. 1 is a diagrammatic view of a person having their skin photographed in a skin imaging station which incorporates the calibration apparatus of the present invention.

FIG. 1 shows a skin imaging station 10 having the features and functionality described in applicants' co-pending U.S. patent application Ser. No. 10/008,753, entitled, "Method of Taking Inages of the Skin Using Blue Light and the Use Thereof", which was published as United States Application Publication No. US 2004/0146290 A1, U.S. patent application Ser. No. 10/978,284 entitled "Apparatus for and Method of Taking and Viewing Images of the Skin," which was published as United States Patent Application Publication No. US 2005/0195316 A1 ("U.S. Publication No. 2005/0195316"), application Ser. No. 11/169,813 entitled "Skin Imaging System with Probe", which was published as United States Application Publication No. US 2006/0092315 A1 ("U.S. Publication No. 2006/0092315"), all of which are incorporated by reference herein in their entirety. U.S. Publication Nos. 2005/0195316 and 2006/0092315 describe the use of alternative illuminating techniques to highlight and emphasize skin conditions, such as wrinkles or acne, wherein a flash unit which is capable of producing light of a particular wavelength is activated and an image captured with a camera. Various filters may also be employed in this process.

One technique described in the above referenced applications involves taking a blue fluorescence photograph of a subject's skin to illuminate and reveal skin conditions such as acne and "horns" (i.e., mixtures of sebaceous lipids, keratinocytes, and possibly sebocytes impacted in open comedones and blackheads on the skin) by producing bright images of the distribution of coproporphyrin, a substance associated with these conditions. By using substantially only blue light (i.e., light having a wavelength ranging from about 375 to about 430 nm), the fluorescence emission of coproporphyrin is maximized. Excitation in the blue region of the spectrum therefore yields bright fluorescence emission images of the distribution of horns.

Blue fluorescence photography typically uses filters having a very narrow bandwidth, and the resulting attenuation requires the use of high-intensity light sources (e.g., flashes). However, high intensity light sources are prone to fluctuations in intensity and color temperature, which may result in inconsistent images. These inconsistencies may also result from slight fluctuations of the power source or environmental factors, such as accidental light exposure from another source (e.g., outside light from opening the door of the room in which the subject is being imaged). Such inconsistencies may appear in successive photographs taken of the subject, if the light intensity of the flash varies between the taking two or more photographs. As a result, images of a subject's skin that are not taken under substantially identical lighting conditions may vary, which adversely affects the quality and/or consistency of the images obtained and compromises the information gleaned therefrom. Therefore, there is a need for a fluorescence standard to aid in interpreting each photograph, to compare light intensity levels of successively-taken photographs, to adjust for varying incident light intensity and to provide a standard reference for calibration.

As shall be apparent from the following, the present invention could be utilized to calibrate other imaging systems, but the referenced system may be used to illustrate the present invention. The skin imaging station 10 has a chin rest 14 for supporting a subject S's chin during the imaging process. A camera 16 is mounted in imaging station 10 across from the chin rest 14 and the subject S. The distance between chin rest 14 and the front end of the lens of camera 16 and the camera zoom setting is adjusted so that the subject S's face substantially fills the "frame" of camera 16, the chin rest 14 positioning the subject in a consistent orientation and distance from the camera 16. One or more blue flash units 18a (only one of which is shown, for the sake of clarity), which are used for blue fluorescent photography, are mounted in the imaging station 10 to illuminate the face of the subject S. A blue filter 18b is placed in front of each blue flash unit 18a. A power pack (not shown) is provided to power blue flash units 18a. Blue flash unit 18a is directed toward the center of the subject S's face. Other flash units, and their associated filters and power packs, may also be mounted in the imaging station 10 for standard and other types of photography (see U.S. Publication No. 2005/0195316).

Still referring to FIG. 1, skin imaging station 10 further includes a display monitor 20 operably connected to a computer (not shown) housed in imaging station 10. More particularly, the computer runs software programs that operate monitor 20, camera 16, flashes, e.g., 18a and a user interface. After the subject S has entered his or her relevant biographical and medical information using monitor 20 and is ready to be photographed, the operating software makes a function call to imaging acquisition and display software ("IFDL software") (IDL Research Systems, Inc., Boulder, Colo.). The IDL software then triggers camera 16 to acquire blue fluorescence photographs (as well as other types of photographs, if desired). Flash unit 18a is triggered through the use of radio transceivers (see U.S. Publication No. 2005/0195316), a custom made flash sequencer, a programmable logic controller or "flash distributor". Prior to taking the blue fluorescence photographs, the IDL software moves long pass filter 24 (Kodak Wratten No. 8 or 12, Eastman Kodak, Rochester, N.Y.) in front of the lens of camera 16. The blue fluorescence photographs are then taken. After the photographs are taken, the IDL software triggers the servo motor 22, solenoid or filter wheel to move long pass filter 24 away from the lens of camera 16.

Figure 2:
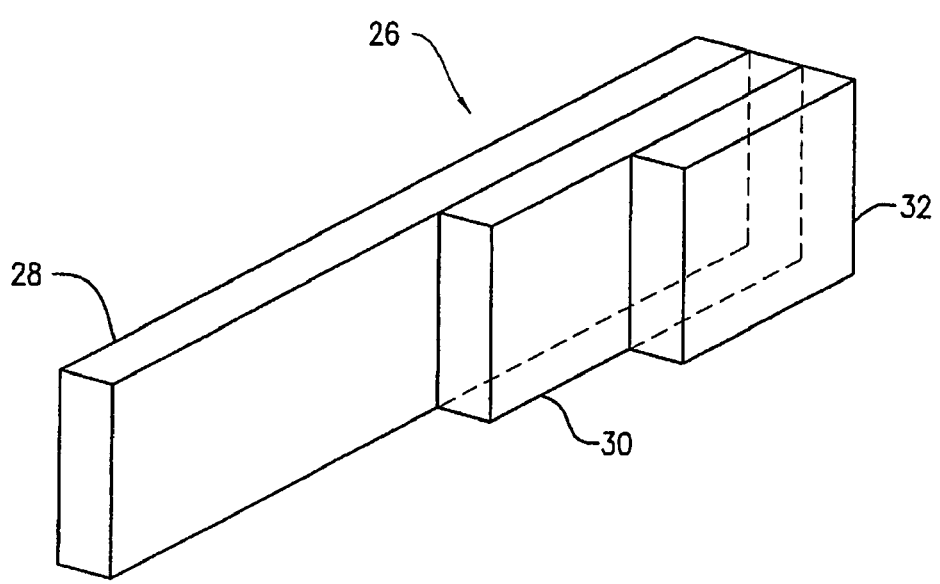
FIG. 2 is a perspective view of the calibration apparatus shown in FIG. 1, wherein the calibration apparatus is shown separate from the skin imaging system to facilitate consideration and discussion.

Now referring to FIGS. 1 and 2, a calibration standard 26 is mounted on chin rest 14 (e.g., in a slot provided therein) in the present embodiment such that when the subject S positions their chin in the chin rest 14, the calibration standard 26 is positioned proximate to their face (see FIG. 1). The calibration standard 26 has two or more overlapping layers, and is shown in FIG. 2 as having three such layers 28, 30 and 32, respectively. The first layer 28 is fabricated from GG420 filter glass (Schott Glass Technologies Pa., Duryea,) a material having fluorescence (excitation and emission) properties similar to that of skin when exposed to UV or blue light, i.e., light having a wavelength of about 375-430 nm. The second layer 30 has a smaller area than that of first layer 28, and partially overlays first layer 28 (see FIG. 2). The second layer 30 is fabricated from BG39 filter glass (Schott Glass Technologies Pa., Duryea,) a translucent, non-fluorescent material that acts as an attenuating layer. The third layer 32 is similar to second layer 30 in that it is also fabricated from BG39 filter glass and also acts as an attenuating layer. The third layer 32 has a smaller area than that of first and second layers 28, 30, and partially overlays second layer 30 (see FIG. 2). The second and third layers 30, 32 progressively reduce the fluorescence intensity of first layer 28. The three layers 28, 30, 32 may be held together in a stacked configuration by a plastic housing (not shown). This layered assembly may be removeably attached to the imaging system 10 to allow removal for storage to protect the standard 26 from damage and contamination. Various standards 26 can be used with an imaging station 10 for different imaging sessions.

FIGS. 3A and 3B show images 34a and 34b, respectively, of the subject S and calibration standard 26, as shown on skin imaging station monitor 20. During the blue light imaging of the subject S, as fully described in U.S. Publication No. 2005/0195316, the three layers 28, 30 and 32 of calibration standard 26 receive blue light of the same intensity as that which illuminates the subject S's face. The portion of first layer 28 exposed to the blue light (i.e., the area not covered by second and third attenuating layers 30, 32), has a fluorescence response similar to skin. The second layer 30 has an attenuating effect on the fluorescence of first layer 28, reducing the amount of fluorescence produced in response to the blue light. The third layer 32, when combined with second layer 30, has a greater attenuating effect on the fluorescence of first layer 28, further reducing the amount of fluorescence produced in response to the blue light. By absorbing the blue light and fluorescing at different, consistent, known levels, the three layers 28, 30, 32 function as three fluorescence standards to provide multiple reference standards for calibration. A software routine may be used to determine the location of the fluorescence standards in images 34a and 34b, analyze the returning light intensity from the standards incorporated in apparatus 26, and calibrate the system based on this analysis, as described hereinbelow.

Both of the images 34a and 34b are formed by two-dimensional matrices of pixels. Every pixel occupies a unique (X,Y) location in a matrix and has an intensity value. In each of FIGS. 3A and 3B, the locations of three sample pixels are illustrated, viz., a pixel located in the area representative of third layer 32 of the standard 26 on the images 34a and 34b with location ($X_1, Y_1$), and two pixels at areas representative of the subject S's skin having locations ($X_2, Y_2$) and ($X_3, Y_3$). Image 34a is taken at a time $T_1$, while image 34b is taken at time $T_2$. The time each image was taken is denoted with the location coordinates in the images (e.g., ($X_1, Y_1, T_1$) in the image 34a and ($X_1, Y_1, T_2$) in the image 34b).

When a series of successive photographic images such as 34a and 34b is taken of a subject S, fluctuations in illumination (flash) light intensity described above may occur between the times $T_1$ and $T_2$, resulting in different light intensity values for the pixels in the areas representative of the standard 26, e.g., at ($X_1, Y_1$), as well as the subject S's skin, e.g., at ($X_2 Y_2$). Varying light intensity of pixels representative of the standard 26 is an indicator that the illumination light has varied. Accordingly, one of the aspects of the present invention is to identify the situation where the illumination light intensity has varied between at least two digital images taken in such varying illumination light. Without the use of the standard, it would not be possible to attribute the difference in light intensity values between one or more pixels, e.g., at ($X_2, Y_2$) in successive images of the skin (e.g., 34a and 34b) to such illuminating light fluctuations, or to varying skin conditions exhibited by the subject S at times $T_1$ and $T_2$.

In order to discern intensity variations in the image area corresponding to the standard 26, that area in the images, e.g., 34a, 34b must be identified/isolated so that the intensity values of the correct pixels can be identified. This may be done by assigning a pre-determined region of the image to the standard 26. More particularly, if the focus setting and orientation of the camera 16 remains fixed, then the standard 26 will appear in the same areas of each image taken, such that the image area corresponding to the standard 26 (and subparts 28, 30, 32) can be empirically determined and remains constant. Alternatively, the image can be scanned (entirely or a subset of pixels, e.g., one of every 50 pixels) to test for repeating intensity values in the form of a rectangle (having a rectangular shape). In the case of a multipart standard 26, like that shown in FIG. 2, the presence of more than one adjacent rectangle (here three) each with consistent intensity values, (progressively decreasing for each area 28, 30, 32) is a reliable indicia of locating the standard 26. Scanning for the standard 26 has the advantage that movement of the standard in the image, e.g., due to movement or focus change of the camera 16 will not result in erroneous readings for the standard.

Having located the pixels representing the standard 26 in the images 34a, 34b, the light intensity values of corresponding pixels, e.g., ($X_1, Y_1, T_1$) and ($X_1, Y_1, T_2$) can be compared. Subtracting one intensity value, e.g., at ($X_1, Y_1, T_1$) from the other, e.g., at ($X_1, Y_1, T_2$) yields a number representing the quantified difference in intensity between the pixels. Alternatively, more sophisticated analyses of the intensity differences between the images can be effected that are non-linear, e.g., gamma curves or conversion into alternate colorspaces, particularly for large differentials. In conducting numerical analysis of digital images, e.g., 34a, 34b, it is frequently beneficial to convert the image from RGB format to L*a*b* format in order to simplify the mathematics and gain greater insight into the color composition and brightness of the images.

Given the identification (and quantification) of illumination light variation between images taken at different times, as determined by the present invention, optional remedial steps maybe taken: (i) correct the environmental conditions of the imaging, e.g., instructing an operator to eliminate extraneous environmental lighting input, e.g., from an open door or shade, repositioning the subject, etc. (ii) adjust/correct the source of illumination, e.g., the light 18a, e.g., by repositioning it, replacing it with another or electronically adjusting its output, e.g., by adjusting the voltage input to the light; or (iii) normalizing the relevant image by adjusting the intensity values of all pixels in the image relative to the image selected as the reference image, e.g., globally adding or subtracting the quantified intensity difference identified by comparing the difference in intensity attributable to the portion of the images representing the standard 26 (and saving the normalized/corrected image for comparison). For example, if the image intensity of a second image is less than a first image by a value of "5" (due to a variation in illumination intensity as determined by the image intensity of the standard 26 appearing in each image) then the second image can be normalized to the first by adding "5" to the pixel intensity of all pixels in the second image. Alternatively, more sophisticated analyses of the intensity differences between the images can be effected that are non-linear, e.g., gamma curves or conversion into alternate colorspaces, particularly for large differentials. With respect to the first two options, i.e., adjusting the environment or the illuminating light, the image with variations is discounted and a new image is taken. With the third option of adjusting intensity values, the image need not be retaken.

It should be appreciated that the process of normalizing can be conducted with reference to the standard 26 image intensity values taken from any arbitrary image, e.g., 34a or 34b, since the process of adjustment is relative, and that the process of normalization can be conducted for any number of images ranging from 1 to any number N. The normalized image(s) may then be displayed or stored with other images in the computer memory or a file.

It should be understood that the embodiment of FIGS. 1-3B is merely exemplary, and that a person skilled in the art may make many variations and modifications without departing from the spirit and scope of the invention. For instance, more or fewer attenuating layers may be included in the calibration apparatus 26. While the present invention has been explained in the terms of adjusting for variations in blue illumination light, the present invention could also be utilized to identify and compensate for variations in illuminating light of other wavelengths. All such variations and modifications are intended to be included within the scope of the invention.

We claim:

1. A fluorescence standard for identifying variations in illumination by a light source emitting light in the approximate wavelength range of 375 nm to 430 nm during imaging of the facial skin of a person with a camera conducted at a plurality of times, comprising: a fluorescent standard, which fluoresces in response to light in the approximate wavelength range of 375 nm to 430 nm, said fluorescent standard having two areas with different fluorescent response, a first area formed from a filter glass of a first type in a first layer and having a fluorescent response to light in the approximate wavelength range of 375 nm to 430 nm and a second area formed from a filter glass of a second type in a second layer partially covering said first layer and attenuating the fluorescent response of said first layer in the area of overlap, a holder for holding said standard near the facial skin of the person in a substantially reproducible spacial relationship between said camera, said standard and said facial skin, permitting said standard and the facial skin of the person to be similarly and simultaneously illuminated by the light in the approximate wavelength range of 375 nm to 430 nm and to be photographed by said camera at each of the plurality of times of imaging.

2. The standard of claim 1, wherein said first type of filter glass is GG420 filter glass and said second type of filter glass is BG39 filter glass.

3. The standard of claim 1, wherein said holder holds said first and second layers in a stacked configuration.

4. The standard of claim 3, wherein said holder has a chin rest for establishing the position of the person for imaging.

5. The standard of claim 4, wherein said standard is mountable on said chin rest proximate the person.

6. The standard of claim 1, further comprising a third layer of material partially covering said second layer, said third layer further attenuating the fluorescence of the first layer beyond that attenuation attributable to said second layer.

7. A method for identifying variations in illumination by a light source emitting light in the approximate wavelength range of 375 nm to 430 nm during imaging of the facial skin of a person with a camera, comprising the steps of
- (A) obtaining a fluorescent standard, which fluoresces in response to light in the approximate wavelength range of 375 nm to 430 nm;
- (B) positioning the fluorescent standard before the camera and the light source;
- (C) positioning the person before the camera and the light source and adjacent to the fluorescent standard;
- (D) simultaneously capturing a first image of the person and the fluorescent standard by illuminating both simultaneously with light in the approximate wavelength range of 375 nm to 430 nm;
- (E) subsequent to said step (D), substantially recreating the relative positioning of the fluorescent standard, the camera, the light source and the person as was previously done in steps (B) and (C);
- (F) capturing a second image of the person and the fluorescent standard with light in the approximate wavelength range of 375 nm to 430 nm;
- (G) identifying a portion of the first image and the second image representing the fluorescent response attributable to the fluorescent standard in the first and second images;
- (H) comparing the fluorescent response of the fluorescent standard in the first image to the fluorescent response of the fluorescent standard in the second image;
- (I) in the event that there is a significant difference in fluorescent response ascertained in (H), then remediating at least one of the first image and the second image to reduce the difference.

8. The method of claim 7, wherein said step (G) of identifying is by programmatically testing the first and second images for areas meeting criteria indicative of the fluorescent standard.

9. The method of claim 8, wherein the criteria includes shape.

10. The method of claim 9, wherein the criteria includes size.

11. The method of claim 7, wherein said step of identifying is by manually ascertaining the location of the fluorescent standard in the first image and imaging in the approximate same manner for the second image, such that the fluorescent standard occupies substantially the same position in each of the first and second images.

12. The method of claim of 7, further comprising the step of retaking at least the second image if a variation in illumination is noted to have occurred.

13. The method of claim 12, wherein the step of remediating includes remediating illumination conditions before said step of retaking, including at least one of adjusting an illuminating apparatus, repairing the illuminating apparatus, adjusting the camera, repairing the camera, and adjusting ambient lighting conditions.

14. The method of claim 12, wherein the first and second images are digital images, a variance of illumination has been noted as having occurred and wherein said step of remediating includes the step of normalizing the first and second images by digitally processing at least one of the images.

15. The method of claim 7, wherein the first and second images are digital images and further comprising the step of converting the first and second digital images from a first colorspace to another colorspace before said step of comparing.

16. The method of claim 15, wherein a variance of illumination has been noted as having occurred and wherein said step of remediating includes the step of normalizing the first and second images by digitally processing at least one of the images expressed in said another color space and then converting back to the first colorspace.

* * * * *